(12) United States Patent
O'Neill et al.

(10) Patent No.: US 10,987,249 B2
(45) Date of Patent: Apr. 27, 2021

(54) METHOD AND SYSTEM FOR GENERATION OF CUSTOMISED SENSORY STIMULUS

(71) Applicant: NEUROMOD DEVICES LIMITED, Belfield, Dublin (IE)

(72) Inventors: Ross O'Neill, Dublin (IE); Caroline Hamilton, Dublin (IE); Stephen Hughes, Dublin (IE)

(73) Assignee: Neuromod Devices Limited, Dublin (IE)

( * ) Notice: Subject to any disclaimer, the term of this patent is extended or adjusted under 35 U.S.C. 154(b) by 1374 days.

(21) Appl. No.: 14/915,559

(22) PCT Filed: Aug. 28, 2014

(86) PCT No.: PCT/EP2014/068256
§ 371 (c)(1),
(2) Date: Apr. 14, 2016

(87) PCT Pub. No.: WO2015/028549
PCT Pub. Date: Mar. 5, 2015

(65) Prior Publication Data
US 2017/0042739 A1    Feb. 16, 2017

(30) Foreign Application Priority Data
Aug. 30, 2013    (EP) .................................... 13182487

(51) Int. Cl.
*A61F 11/00*    (2006.01)
*A61B 5/00*    (2006.01)
(Continued)

(52) U.S. Cl.
CPC .............. *A61F 11/00* (2013.01); *A61B 5/128* (2013.01); *A61B 5/7455* (2013.01); *A61F 11/04* (2013.01);
(Continued)

(58) Field of Classification Search
CPC .......... A61F 11/00; A61F 11/04; A61H 23/02; A61H 2205/027; A61B 5/128;
(Continued)

(56) References Cited

U.S. PATENT DOCUMENTS 5,788,656 A * 8/1998 Mino ...................... A61F 11/00
601/47
2001/0031996 A1* 10/2001 Leysieffer .......... A61N 1/36036
607/57
(Continued)

FOREIGN PATENT DOCUMENTS

WO    2006/130909 A1    12/2006
WO    2012/069429 A1    5/2012

OTHER PUBLICATIONS

Arnaud J. Norena et al., "Enriched Acoustic Environment After Noise Trauma Abolishes Neural Signs of Tinnitus", NeuroReport, Apr. 24, 2006, pp. 559-563, vol. 17 No. 6, Canada.
(Continued)

*Primary Examiner* — Tu A Vo
(74) *Attorney, Agent, or Firm* — Schmeiser, Olsen & Watts LLP

(57) ABSTRACT

A tinnitus treatment system is provided. The system includes a sound processing unit, a haptic stimulus unit and an audio delivery unit. The sound processing unit includes a processor input for receiving an audio signal; and a digital signal processor to analyze the audio signal and generate a plurality of actuation signals therefrom which are representative of the audio signal. The digital signal processor may spectrally modify the audio signal in accordance with a predetermined modification profile to generate a modified audio signal. The haptic stimulus unit includes an array of stimulators each of which independently apply a tactile stimulus to a subject; and a stimulus unit input receives the plurality of actuation signals generated by the digital signal processor and directs
(Continued)

individual actuation signals to individual stimulators. The audio delivery unit includes an audio delivery unit input for receiving the modified audio signal generated by the digital signal processor.

19 Claims, 10 Drawing Sheets

(51) Int. Cl.
| | |
|---|---|
| *A61M 21/00* | (2006.01) |
| *A61H 23/00* | (2006.01) |
| *A61B 5/12* | (2006.01) |
| *H04R 25/00* | (2006.01) |
| *A61F 11/04* | (2006.01) |
| *A61H 23/02* | (2006.01) |
| *G10L 21/06* | (2013.01) |

(52) U.S. Cl.
CPC ............. *A61H 23/02* (2013.01); *A61M 21/00* (2013.01); *H04R 25/75* (2013.01); *A61H 2205/027* (2013.01); *A61M 2021/0027* (2013.01); *G10L 2021/065* (2013.01)

(58) Field of Classification Search
CPC ...... A61B 5/7455; H04R 25/75; A61M 21/00; A61M 21/02; A61M 2021/0027; G10L 2021/065
See application file for complete search history.

(56) References Cited

U.S. PATENT DOCUMENTS

| | | | |
|---|---|---|---|
| 2002/0090100 A1* | 7/2002 | Thiede | A61F 11/00 381/314 |
| 2005/0201574 A1* | 9/2005 | Lenhardt | A61H 23/0245 381/151 |
| 2008/0137873 A1* | 6/2008 | Goldstein | H04R 1/1016 381/57 |
| 2011/0054241 A1* | 3/2011 | Jensen | H04R 25/75 600/28 |
| 2012/0308060 A1* | 12/2012 | Pontoppidan | H04R 25/505 381/317 |
| 2013/0184552 A1* | 7/2013 | Westermann | A61B 5/0006 600/378 |
| 2016/0038712 A1* | 2/2016 | Finsterle | H04S 1/00 600/28 |

OTHER PUBLICATIONS

Michael P. Kilgard et al., "Cortical Map Reorganization Enabled by Nucleus Basalis Activity", Science-American Association for the Advancement of Science, Mar. 13, 1998, pp. 1713-1718, vol. 279, Washington D.C.

International Searching Authority, "Search Report with Written Opinion of the International Searching Authority for PCT/EP2014/068256", dated Mar. 5, 2015, Munich.

* cited by examiner

METHOD AND SYSTEM FOR GENERATION OF CUSTOMISED SENSORY STIMULUS

FIELD OF THE INVENTION

The present invention relates to the generation of customised sensory stimulus for delivery to a patient suffering from a hearing impairment. The invention is particularly related, but not limited to the field of delivery of customised multi-sensory tinnitus treatment.

BACKGROUND TO THE INVENTION

Tinnitus is an abnormal neurological behaviour arising from loss of signal through the ear. While the precise causes of tinnitus are not fully understood, certain analogies are employed to describe the likely causes. It is believed that tinnitus is often caused by a physical hearing impediment such as damage to the hair cells in the cochlea. In an attempt to compensate for the missing audio information the brain raises amplification in deficient channels to such an extent that noise in the channel, otherwise described as resting or homeostatic firing rates, is amplified above the perceptual threshold and perceived as illusory sound. Alternatively, one may imagine an electrical water pump whose water supply is suddenly restricted. The pump oscillates and vibrates in a desperate attempt to compensate for the loss of input. Certain forms of tinnitus may be thought of as essentially arising from the same types of mechanism: loss of signal through the ear results in increased gains resulting in spontaneous and oscillatory activity in the associated neurons in the brain. This activity is perceived as illusory sound by the sufferer.

Tinnitus sufferers are significantly more likely to perceive an illusory audio after-effect known as the Zwicker Tone. The Zwicker Tone is induced by exposing the individual to broad-spectrum noise (20 Hz-20 KHz) with a spectral gap (silence) at an arbitrary frequency. When the noise is removed the individual perceives a 'ringing' at the frequency of the spectral gap. This suggests that in order to compensate for the unequal cochlear sensitivity across frequencies, the brain introduces frequency dependent sensitivity or gain similar to a 'graphic equalizer' on a stereo. At the frequencies that our cochlea is less sensitive, the brain increases the gain in that frequency band to compensate. In frequency bands where sensitivity falls below a minimum threshold, the brain increases the gain to pathological levels. This manifests as illusory noise, ringing or even chaotic oscillation, the most commonly described effects of Tinnitus.

A very large number of treatments have been proposed for tinnitus, including radiosurgery, direct stimulation of the auditory nerves, pharmacological treatments, psychological treatments, and treatment by playing external sounds to the patient. While many such treatments provide relief in some groups of patients, at present there is no reliable treatment for all patients, and the present invention aims to provide a further alternative approach.

SUMMARY OF THE INVENTION

One embodiment of the invention provides a tinnitus treatment system comprising a sound processing unit, a haptic stimulus unit and an audio delivery unit: wherein said sound processing unit comprises: a processor input for receiving an audio signal; and a digital signal processor operable to analyse said audio signal and generate a plurality of actuation signals therefrom which are representative of said audio signal, the digital signal processor further being operable to spectrally modify said audio signal in accordance with a predetermined modification profile to generate a modified audio signal; wherein said haptic stimulus unit comprises: an array of stimulators each of which can be independently actuated to apply a tactile stimulus to a subject; and a stimulus unit input for receiving the plurality of actuation signals generated by said digital signal processor and directing individual actuation signals to individual stimulators; and wherein said audio delivery unit comprises an audio delivery unit input for receiving the modified audio signal generated by said digital signal processor. This system has the advantage of delivering a customised audio signal to a patient suffering from tinnitus in such a way that the tinnitus may be treated. Without wishing to be bound by theory, it has been proposed that sound enrichment (inversely proportional to induced hearing loss) may prevent the neuropathologies that give rise to tinnitus. However, many patients do not notice or acknowledge their hearing loss until after the onset of these neuropathologies and the symptoms of tinnitus, and at this stage it may be too late to lastingly treat tinnitus simply through sound enrichment. There is 'mixed' but no comprehensive evidence that hearing aids provide relief from tinnitus, and in some instances it has been found that hearing aids provide only transient rather than enduring relief. The present invention addresses this problem by delivering a stronger signal to the brain by accompanying an audio signal with additional haptic stimulus. In one embodiment of the invention, the haptic stimulus comprises electrotactile stimulus delivered transcutaneously to the tongue. It is believed that the increased dual modality of this signal has a greater chance of triggering neuroplasticity in the brain that may result in a lasting adjustment in the patient that may alleviate the symptoms of tinnitus. In addition to this, by providing sound enrichment that is inversely proportional to the acquired hearing loss, the patient's particular hearing loss profile is directly targeted with a customised treatment.

The system may comprise a digital signal processing apparatus and a stimulus delivery apparatus, wherein the digital signal processing apparatus comprises: the digital signal processor; and an electronic file writer for storing said generated actuation signals and said modified audio signal in an electronic file format; and wherein the stimulus delivery apparatus comprises: said haptic stimulus unit; said audio delivery unit; and an electronic file reader for reading electronic files produced by said digital signal processing apparatus, for converting said files into an audio signal and a plurality of actuation signals, and for delivering said signals to said audio delivery unit and said haptic stimulus unit respectively.

While in other embodiments of the invention it may be desirable to house all of the system components in a single apparatus and to perform the digital signal processing dynamically (i.e. on the fly), in this embodiment of the invention, the digital signal processing may be performed in advance. The audio and actuation signals may be written to an electronic file format for later use. In one embodiment of the invention the electronic file format may be a customised analog of the .wav format with two separate audio channels (one customised for each ear) and a third channel for storing the actuation signalling. This file may then be stored on a transferable medium or otherwise transmitted to the stiumlus delivery apparatus, which can then be used to read the file and generate the signals to apply the treatment. Separation of the signal processing and signal delivery elements of the invention allows for the reduction of unit costs because fewer digital signal processing apparatuses may need to be produced, and also allows for greater ease of maintenance of the stimulus delivery apparatuses as they are comprised of less complex component parts.

In an embodiment of the invention, the sound processing unit further comprises a preprocessing module, the preprocessing module comprising: a first preprocessor input for receiving a first audio signal component; a second preprocessor input for receiving a second audio signal component; an adder, for combining the first audio signal component with the second audio signal component into a preprocessed audio signal, and a preprocessor output, for delivering the preprocessed audio signal to the processor input.

Such a system is advantageous because it allows different audio signals having different properties to be combined to synergetic beneficial effect. The first audio signal component may comprise comparatively "broad-spectrum" noise that spans the patient's hearing loss spectrum range. The modified signal is amplified at different frequencies to an amount proportional to the hearing loss at each frequency, thereby delivering a customised stimulus to the listener. In this way, the sound enrichment provided is specific to the listener and covers all frequencies of the individual's hearing loss. Such broadband noise as may be suited to this purpose may comprise "coloured noise". Coloured noise in the context of audio systems is any noise signal that is not white i.e. it is any noise that is not spectrally uniform. For the purposes of this technology, coloured noise is used to describe the noise that is created to deliberately compensate for the deficit in the patient's hearing profile, with the Result the patient perceives white (i.e. spectrally uniform) noise. This is usually achieved by applying a filter to shape a white noise signal, the shape of the filter being the inverse of the patient's audiogram. For example, an audio white noise source will not actually be perceived as white (flat) by a person with normal hearing, due to the fact that normal hearing sensitivity thresholds increase at frequencies above and below about 1 kHz. Grey noise is noise that has been spectrally shaped as the inverse to the normal hearing profile, and is thereby perceived as white noise by a person of normal hearing. In addition, green noise is noise that has been band-boost filtered to occupy the spectral bandwidth of speech (typically 100 Hz to 8 kHz). Grey noise, green noise or derivatives thereof may be used as the broad band signal in embodiments of this invention. Of additional advantage is the addition of a second audio signal component that may be designated an "attentional sound component". This second audio signal component should preferably be relatively complex, both in terms of temporal and frequency characteristics, in such a way as to engage the listener. For example a musical piece (such as a piano piece) or a spoken word recording (preferably with softly-spoken speech) would be suitable. It is necessary that this signal be relatively relaxing in terms of amplitude, so as not to exacerbate the emotional state of the patient. Audio signals of this nature have the capability of commanding the attention of the listener, and—without wishing to be bound by theory—it is attention is key to driving neuroplasticity. Accordingly, the addition of a broad-spectrum noise signal that covers the range of the patient's hearing loss to a signal comprising an attentional sound component has the synergetic effect of commanding the patient's attention and thus driving neuropasticity, while at the same time delivering a modified signal over the whole range of hearing loss in order to try to comprehensively drive adaption within the brain, that combats tinnitus.

Another embodiment of the invention comprises a tinnitus treatment system comprising a sound processing unit comprising a preprocessing module, wherein the preprocessing module comprises: a first preprocessing input for receiving a first audio signal component; a second preprocessing input for receiving a second audio signal component; an adder, for combining the first audio signal component with the second audio signal component into a preprocessed audio signal, and a preprocessor output, for delivering the preprocessed audio signal to a processor input of the sound processing unit; and wherein the sound processing unit further comprises: a processor input for receiving the preprocessed audio signal output from the preprocessing unit; a digital signal processor operable to spectrally modify said preprocessed audio signal in accordance with a predetermined modification profile to produce a modified audio signal; a processor output for receiving said modified audio signal from said digital signal processor.

The system may comprise a noise generator, wherein the noise generator is configured to generate an audio signal and deliver said audio signal to said first preprocessor input.

In one embodiment of the invention, the digital signal processor further comprises a band boost filter calibrated in accordance with the predetermined modification profile, and the digital signal processor is operable to spectrally modify said audio signal by passing said audio signal through said band boost filter to produce said modified audio signal.

The predetermined modification profile may be based on an inversion of an audiogram of a patient suffering from tinnitus.

In one embodiment of the invention, the modified audio signal comprises at least a first component signal which occupies a spectral bandwidth that spans the spectral range over which the patient's hearing is impaired.

In another embodiment of the invention, the first component signal occupies a spectral bandwidth that extends beyond the spectral range over which the patient's hearing is impaired most preferably by at least one octave, more preferably extending below the minimum frequency of hearing loss and extending above the maximum frequency of hearing loss each by about half an octave, and preferably extending below the minimum frequency of hearing loss and extending above the maximum frequency of hearing loss each by about quarter of an octave.

In an embodiment of the invention, the modified audio signal occupies a spectral bandwidth such that the modified audio signal, when listened to by said patient elicits the perception of an audio signal comprising at least a white noise component to said signal.

In another embodiment, the modified audio signal comprises at least a first component signal that occupies a spectral bandwidth of between 2 kHz and 6 kHz, more preferably between 500 Hz and 8 kHz, even more preferably between 125 Hz and 20 kHz, and most preferably between 125 Hz and 40 kHz.

In embodiments of the invention comprising first and second audio signal components, the second audio signal component may be capable of holding the attention of a human listener, and is optionally a recording of a musical piece or a recording of human speech.

One embodiment of the invention comprises the digtal signal processing apparatus as previously described and another embodiment of the invention comprises the stimulus delivery apparatus as previously described.

An embodiment of the invention comprises a method of processing an audio signal, comprising: analysing said audio signal; generating a plurality of actuation signals therefrom which are representative of said audio signal, said plurality of actuation signals comprising a first output signal and being suitable for actuation of an electrode array; and spectrally modifying said audio signal in accordance with a predetermined modification profile to generate a modified audio signal, said modified audio signal comprising a second output signal, wherein the output signals are transmitted to signal output devices or converted into an electronic file format and stored electronically; and wherein the method optionally further comprises the step of preprocessing the audio signal by combining a first audio signal component with a second audio signal component into a preprocessed audio signal.

Another embodiment of the invention comprises a method of processing an audio signal comprising: preprocessing the audio signal by combining a first audio signal component with a second audio signal component into a preprocessed audio signal, spectrally modifying said audio signal in accordance with a predetermined modification profile to generate a modified audio signal, wherein the predetermined modification profile is based on an inversion of an audiogram of a patient suffering from tinnitus, and said first audio signal occupies a spectral bandwidth that spans the spectral range over which the patient's hearing is impaired.

One embodiment of the inveniton comprises a method of treating tinnitus comprising any of the methods previously described.

One aspect of the invention comprises an apparatus for use in treating tinnitus, comprising a sound processing unit, a tactile (or haptic stimulus) unit, and an interface therebetween, wherein: said tactile unit comprises an array of stimulators each of which can be independently actuated to apply a tactile stimulus to a subject, and an input for receiving a plurality of actuation signals from said interface and directing individual actuation signals to individual stimulators; and said sound processing unit comprises: an input for receiving an audio signal; a digital signal processor operable to analyse said audio signal and generate said plurality of actuation signals therefrom which are representative of said audio signal; and an output for receiving said plurality of actuation signals from said digital signal processor and providing said plurality of actuation signals to said interface.

Preferably, said digital signal processor is further operable to generate said plurality of actuation signals as a time-varying sequence of output array patterns, wherein each output array pattern comprises a set of actuation signals to be applied to the array for a discrete period of time, representative of a discrete time sample of the input signal.

According to one embodiment, said digital signal processor is programmed to analyse said audio signal by dividing said audio signal into a series of frames in the time domain, performing a transform on each frame to generate a set of coefficients representing said frame, and mapping said set of coefficients to a set of actuation signals to be applied to the array.

Said transform performed on each frame is preferably selected from a fourier transform, a short-time fourier transform (STFT), a wavelet transform, a curvelet transform, a gammatone transform and a zak transform.

More preferably, said transform is a fourier transform or a short-time fourier transform, and wherein said signal is sampled at a sampling rate of at least 24 kHz to cover a bandwidth of between 4 kHz and 12 kHz, optionally a sample rate of 20 kHz to cover a signal bandwidth of between 6 kHz and 10 kHz, and further optionally a sample rate of at least 16 kHz to cover a signal bandwidth up to 8 kHz. This allows the signal to be accurately reconstructed.

Suitably, said time-varying series of frames may overlap with one another. The start of each frame is preferably offset from the start of the preceding frame by between 10 and 20 ms, more preferably by 12-18 ms, and most preferably by about 16 ms. The processor is preferably programmed to employ a frame length of from 18 to 164 ms, more preferably from 50 to 150 ms, and most preferably 64 or 128 ms.

The set of coefficients preferably represent the signal in the frequency domain, and the coefficients are mapped to the actuation signals such that coefficients representing similar frequencies are mapped to actuation signals directed to stimulators which are physically close to one another in said array.

More preferably, the coefficients representing neighbouring frequencies are mapped to actuation signals directed to stimulators which are physically adjacent to one another.

In alternative embodiments, the digital signal processor is programmed to analyse said audio signal by mapping successive segments of said audio signal to a set of features selected from a dictionary of said features.

The array of stimulators can be, for instance, a rectangular arrangement of m×n regularly spaced stimulators, a hexagonal arrangement of concentric hexagonal sub-arrays, or a circular arrangement of concentric circular sub-arrays.

Preferably, said processor is further operable to normalise the magnitudes of the actuation signals to fall within a predetermined range of actuation signal intensities.

In preferred embodiments, said tactile unit is in the form of a body dimensioned to be placed on the tongue of a human subject, and wherein each stimulator is in the form of an electrode having a rounded surface projecting from said body. More preferably, the rounded surface of each electrode is generally hemispherical.

One embodiment uses a tongue-based electrode array as an auditory sensory substitution device, whereby audio information is presented to the brain by way of tactile stimulation applied to the tongue. The system is composed of a wireless electro-tactile display device and an audio processing computer, which wirelessly transmits electro-tactile stimulus images to be displayed—using Bluetooth technology to the electro-tactile display. Alternatively, both components can be combined into a single unit for added portability. Furthermore, the tactile stimulus generated by the system may be presented to any cutaneous surface on the body for that matter.

In other embodiments of the invention, other forms of haptic stimulus may be utilized. Other devices are envisaged that deliver haptic stimulus on the body surface (which has the advantage of being totally transcutaneous and therefore non-invasive), preferably to a location that is innervated by afferent cranial nerves, more preferably that is innervated by afferent trigeminal nerve, and most preferably in a region that has a high density of such afferent nerve fibres. Examples include devices configured to deliver force/pressure stimulus on the surface of the forehead; devices that have a tactile pin array for contact with the surface of the tongue; devices that have a tactile pin array for contact with one or more finger tips (electro-Braille); or devices that have a vibration actuator for contact with the surface of the tongue.

In addition to haptic stimulus, other forms of ancillary stimulus (to accompany audio stimulus) are envisaged. Devices are envisaged that deliver stimulus by way of transcranial electrical stimulation (TES), transcranial magnetic stimulation (TMS), transcranial direct-current stimulation (tDCS) or deep-brain stimulation (DBS) to directly stimulate regions of the brain.

Also devices are envisaged that deliver stimulus by way of implantable nerve stimulators such as Vagus Nerve Stimulation (VNS) and Spinal Cord Stimulators (SNS). Furthermore, devices are envisaged that deliver stimulus by by way of pharmacological neuromodulation agents such as GABA, MDMA, AMPT, SSRIs and Opioid peptides.

In addition to this, further devices are envisaged that deliver ancillary stimulus in the form of visual stimulus. Visual patterns displayed to the patient that could be displayed on a monitor, through eye-wear (i.e. Google Glass), or by flashing lights viewable in the patients peripheral vision.

BRIEF DESCRIPTION OF THE DRAWINGS

Embodiments of the invention will be described, by way of example only, with reference to the accompanying drawings in which.

DETAILED DESCRIPTION OF THE DRAWINGS

Characterization of Hearing Loss

Hearing loss is categorised as being either of the conductive or sensorineural type, whilst mixed hearing loss is generally used to describe cases in which both sensorineural and conductive hearing loss co-exist in the same ear. Conductive hearing loss tends to be mechanical in origin where sound is not conducted effectively from the outer ear to the middle ear. Discrimination is barely affected and most cases can be resolved via surgery or correct prescriptive amplification.

Sensorineural hearing loss (SNHL) tends to occur when there is damage to the inner ear, or the nerve pathway from inner ear to brain. Discrimination is nearly always reduced. SNHL is the most common type of hearing loss and cannot be rectified medially or surgically. Most cases can be resolved via correct prescriptive amplification. The degree of hearing loss can be classified according to the following table:

TABLE 1

Characterization of degree of hearing loss

| Degree of hearing loss | Hearing loss range (dB HL) |
| --- | --- |
| Normal | −10 to 15 |
| Slight | 16 to 25 |
| Mild | 26 to 40 |
| Moderate | 41 to 55 |
| Moderately severe | 56 to 70 |
| Severe | 71 to 90 |
| Profound | 91+ |

In addition to the type and degree of hearing loss, hearing loss may be regarded as having different configurations. A hearing loss that only affects the high tones would be described as high frequency hearing loss and a hearing loss affecting the low frequencies only would be described as low frequency hearing loss.

Other terminology used in the discussion of hearing loss is as follows. Bilateral hearing loss relates to hearing loss in both ears and unilateral hearing loss relates to hearing loss in one ear. Symmetrical hearing loss means that the degree and configuration of hearing loss are the same in each ear. Asymmetrical hearing loss means the degree and configuration of hearing loss are different in each ear. Progressive hearing loss means that hearing loss becomes worse over time. Sudden hearing loss means hearing loss occurred quickly. Fluctuating hearing loss means hearing loss that changes/fluctuates from time to time. Stable hearing loss means that the hearing loss never changes/remains constant.

Testing of Hearing Loss

Figure 1:
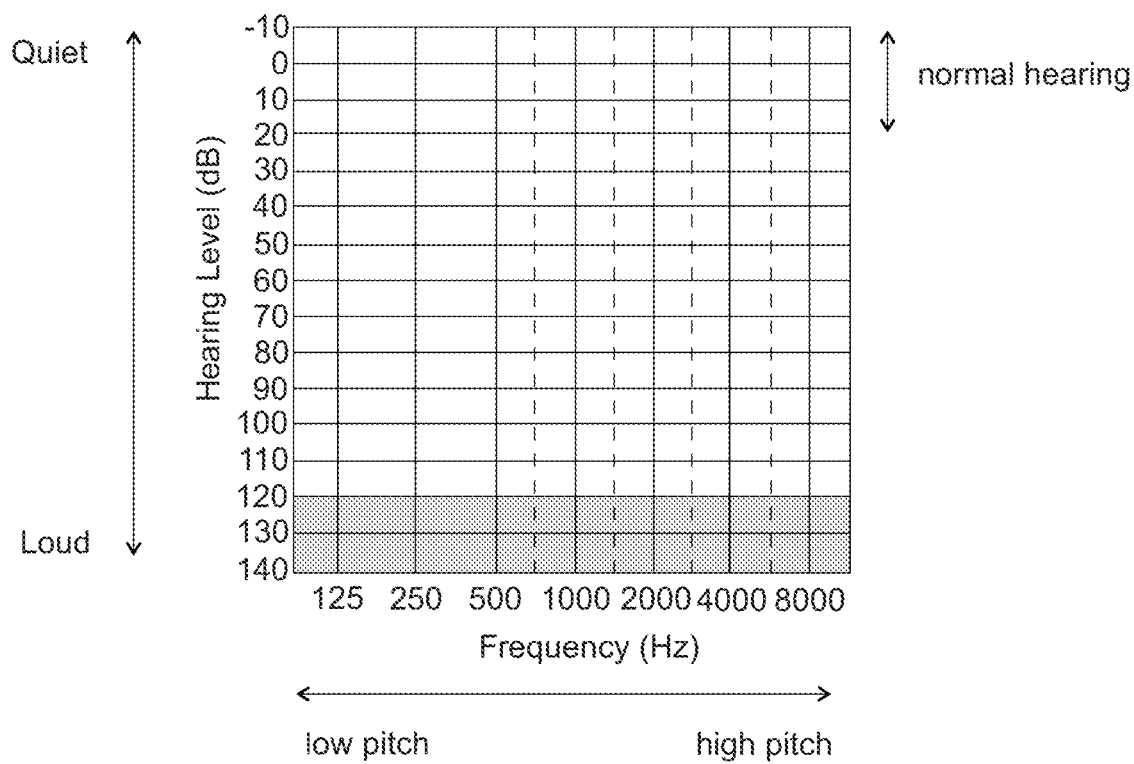
FIG. 1 is a representation of the chart on which an audiogram is produced.

The level of hearing loss of a patient can be measured using an audiogram. The audiogram as illustrated by FIG. 1 is a graph showing the results of the Pure Tone Audiometry (PTA), Automatic audiometry or computerised audiometry tests. It illustrates the Type, Degree and Configuration of hearing loss.

The frequency or pitch of the sound is measured in Hertz (Hz). The intensity or loudness of the sound is measured in decibels (dB). The responses are recorded on the audiogram that shows intensity levels for each frequency tested. The standard set of frequencies tested are a subset of the following frequencies: 125 Hz, 250 Hz, 500 Hz, 1000 Hz, 2000 Hz, 3000 Hz, 4000 Hz, 6000 Hz, 8000 Hz. High frequency testing from: 10,000 Hz, −20,000 Hz is recommended in certain cases.

Pure-tone audiometry, which comprises air-conduction and bone conduction thresholds, is a behavioural test used to measure hearing sensitivity. This measure involves the peripheral and central auditory systems. Pure-tone thresholds (PTTs) indicate the softest sound audible to an individual at least 50% of the time. Responses are recorded on an audiogram (FIG. 1).

In order to test air-conduction, supra-aural earphones or insert earphones are used to transmit stiumuli in the form of continuous or pulsed pure-tone signals. Pulsed tones have been shown to increase a test participant's awareness of the stimuli. The frequencies tested differ, depending on the technique used. Using a diagnostic technique, threshold assessment should be made at 250, 500, 1000, 2000, 3000, 4000, 6000, and 8000 Hz, except when a low-frequency hearing loss exists, in which case the hearing threshold at 125 Hz should also be measured. When a difference of 20 dB or more exists between the threshold values at any two adjacent octave frequencies from 500 to 2000 Hz, interoctave measurements should be made. Appropriate masking should be applied to the non-test ear when the air-conduction threshold obtained in the test ear exceeds the interaural attenuation to the nontest ear (40 dB). If the retest threshold at 1000 Hz differs by more than 5 dB from the first test, the lower of the two thresholds may be accepted, and at least one other test frequency should be retested.

In order to test bone-conduction, a standard bone-conduction vibrator should be placed on mastoid/forehead. Thresholds are obtained at octave intervals from 250 to 4000 Hz and at 3000 Hz. Testing at frequencies below 500 Hz demands excellent sound isolation for cases with normal or near normal sensitivity but may be accomplished when such an environment is available. Higher frequencies may be tested if the transducer has sufficient frequency-response characteristics. If the unmasked bone-conduction threshold is 10 dB better than the air-conduction threshold at that frequency in either ear, masking must be used.

Every audiogram should include the following information: date and location of test; names of participant, audiologist, and, if applicable, referral source; description of test equipment used, including audiometer and transducers, and the audiometric test room; calibration information for equipment used; threshold values for each of the frequencies tested for each ear by air conduction and bone conduction; explanation of all symbols used; observations of physical conditions of the outer ear or other conditions that may have influenced the results and any steps taken to mitigate these conditions; observations of participant behaviour, symptoms, or difficulties; assessment of test reliability; reason for the evaluation; description of alternate test methods or nonstandard test stimuli used, for example "threshold determined by descending presentations method", "pulsed tone substituted", or "warbled tone substituted".

Tinnitus Measurement

Psychoacoustic assessment, including Tinnitus Matching (TM), Tinnitus Loudness Matching (TLM) and Minimum Masking Levels (MML) are determined by establishing the frequency level of the tinnitus and the intensity level of the tinnitus frequency in the contralateral ear or binaurally if there was no difference between both ears. Both measurements are expressed in Hertz (Hz) and Decibels (dB) respectively. When carrying out MML, a broadband noise is introduced and each participant is asked to determine when their tinnitus was inaudible. The MML and TLM is determined using 1 dB steps.

Additional tinnitus test includes, Residual inhibition (RI) which records the amount of time that an individual's noise in the ear(s) is reduced or disappears following a period of masking. The tinnitus is masked for a minimum masking level plus 10 dB for approximately 1 minute.

Inverse Audiogram Filter

The pitch of the phantom sound experienced by a tinnitus sufferer often correlates to the frequency of the hearing loss (i.e hearing loss dip: 30 dB @ 4 kHz and tinnitus matched: 20 dB @ 4 kHz). In one aspect of the invention, the remaining bandwidth in the damaged bands of the cochlea & auditory nerve is stimulated through amplification using band-boost (coloured) noise characterised by the patient's hearing loss. Specifically, the patient's hearing loss (as characterised by an audiogram) is used to produce a predetermined modification profile that is utilized in the generation of the customised band-boost noise. In one embodiment, the predetermined modfication profile is used to produce an "inverse audiogram" band boost filter, and this band boost filter is utilized in the generation of the band-boost noise. This process will now be demonstrated with reference to three illustrative examples.

EXAMPLE 1

In a first example, patient 1 presents with a suspected hearing loss and/or tinnitus, and pure tone audiometry is carried out to quantify the type, degree and configuration of hearing (as described above). Psychoacoustic assessment, including Tinnitus Matching (TM), Tinnitus Loudness Matching (TLM) and Minimum Masking Levels (MML) are determined (as described above).

Figure 2:
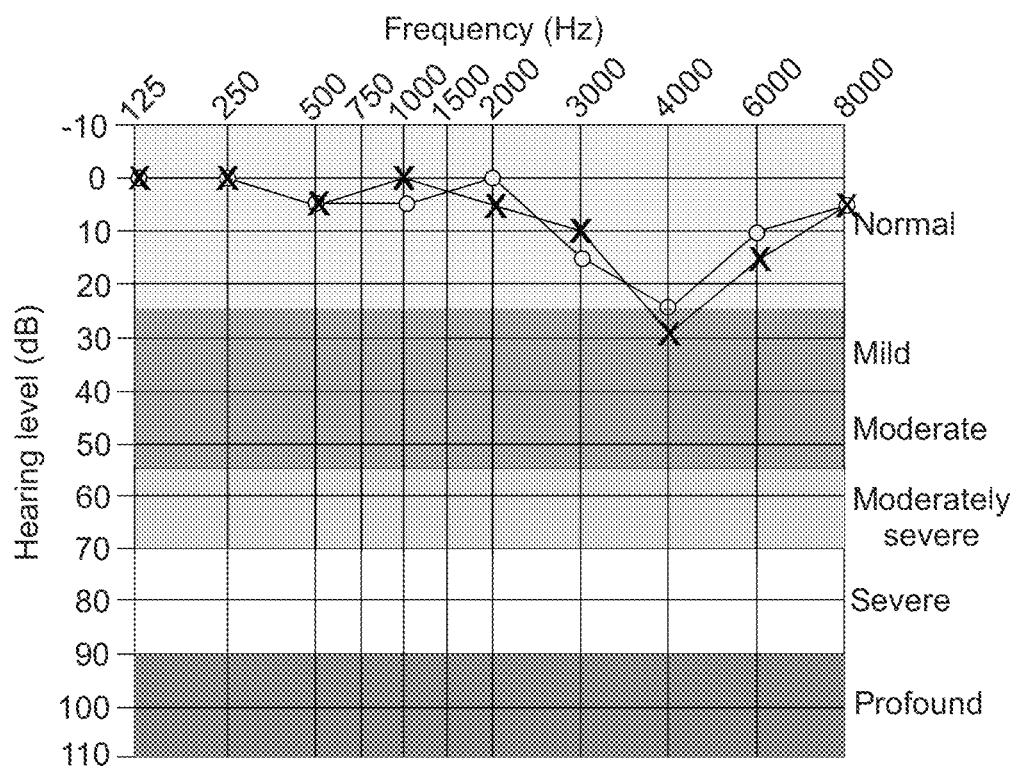
FIG. 2 is a sample audiogram in accordance with patient 1 of example 1.

The results of the audiogram for patient 1 can be seen in FIG. 2 (x=left ear, o=right ear), illustrating bilateral noise induced sensorineural hearing loss displaying a rather simple hearing loss profile. The right ear demonstrates a 25 dB loss at 4 kHz, and the left demonstrates a 30 dB loss at 4 kHz. The results of the psychoacoustic assessment of patient 1 for tinnitus (not shown in FIG. 2) results in tinnitus matched at a pure tone of 20 dB @ 4 kHz for the left ear and no tinnitus for the right ear.

Figure 3:
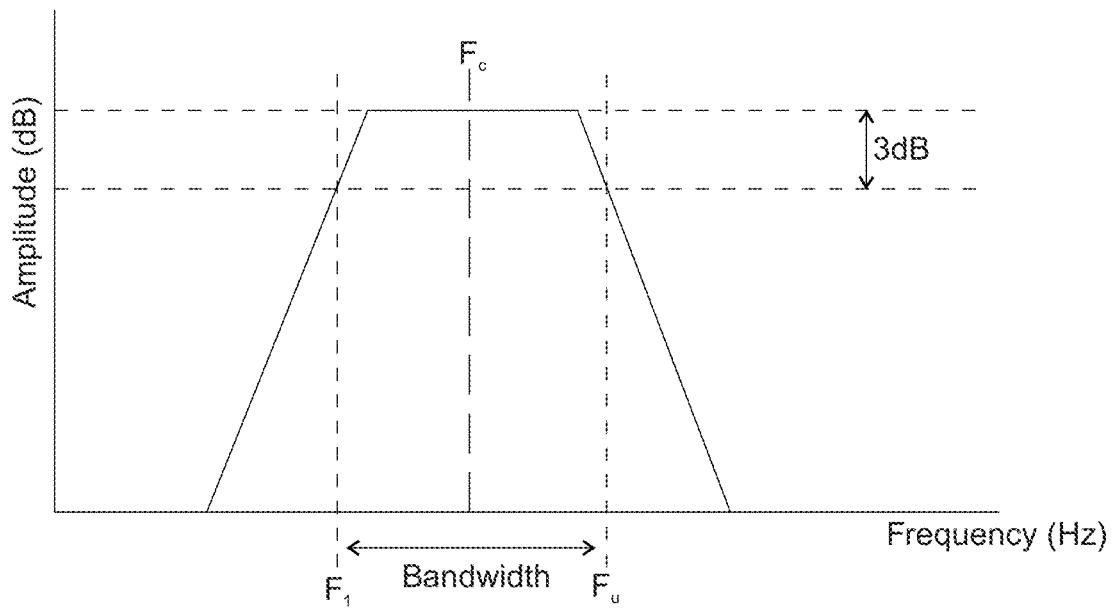
FIG. 3 is an illustrative example of a band boost band boost filter produced in accordance with one embodiment of the invention.

In accordance with an embodiment of the invention, a band boost filter is calibrated to boost certain frequencies (as exemplified in FIG. 3) based on the above hearing loss and tinnitus assessment and applied to an audio signal that is in turn then delivered to the ear. As each ear may have a different hearing loss profile, a different customised signal may be generated for each ear. In this example, a customised signal is only generated for the left ear because no tinnitus has been diagnosed for the right ear. Based on the audiogram, the boost ratio and centre frequency (Fc) may be calculated, and these may be used in the design of the band boost filter. In this example, the boost ratio is set in order to boost by +25 dB, the centre frequency (Fc) identified as 4 kHz (which in this case is also the tinnitus matching frequency). The bandwidth for the filter is determined as one octave up and down from the centre frequency—in this case the bandwidth between the upper and lower cut off frequencies for boosting by the filter is between 2 kHz and 8 kHz (i.e. 6 kHz in range). The slope of the filter is determined as 25 dB/octave (on both the down rising and falling edges). Application of a filter of this type to a patient suffering from this particular hearing loss profile has the effect of normalizing the spectral intensity of the noise that is perceived by the patient. In the event pure white noise is delivered to patient 1 through this filter, patient 1 would perceives the noise as pure white noise.

EXAMPLE 2

In a second example, patient 2 presents with a suspected hearing loss and/or tinnitus, and pure tone audiometry is carried out to quantify the type, degree and configuration of hearing (as described above). Psychoacoustic assessment, including Tinnitus Matching (TM), Tinnitus Loudness Matching (TLM) and Minimum Masking Levels (MML) are determined (as described above).

Figure 4:
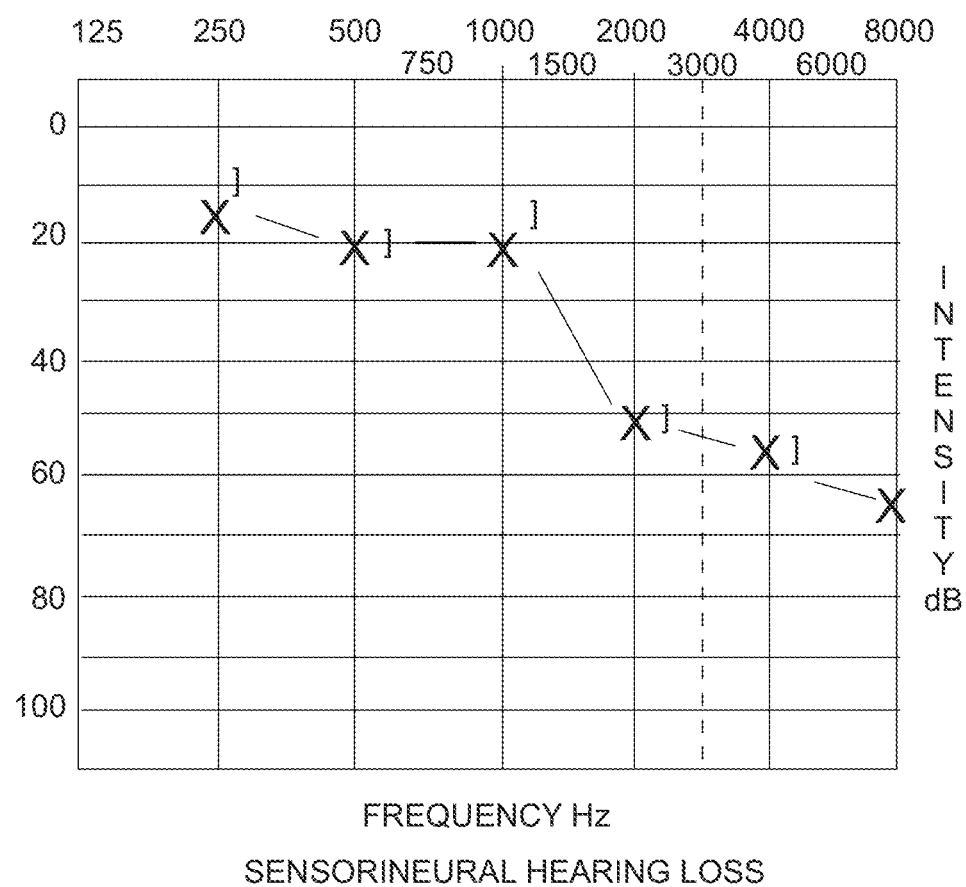
FIG. 4 is a sample audiogram in accordance with patient 2 of example 2.

The results of the audiogram for patient 2 can be seen in FIG. 4, illustrating unilateral high frequency sensorineural hearing loss. The left ear exibits hearing loss as follows: 2 kHz @ 50 dB, 4 kHz @ 55 dB, and 6 kHz @ dB60. The right ear exhibits normal hearing (and is not shown in the audiogram of FIG. 4). The results of the psychoacoustic assessment for tinnitus (not shown in FIG. 4) results in tinnitus matched at a pure tone of 40 dB @ 5 kHz on the left ear, and no tinnitus in the right ear.

Figure 5:
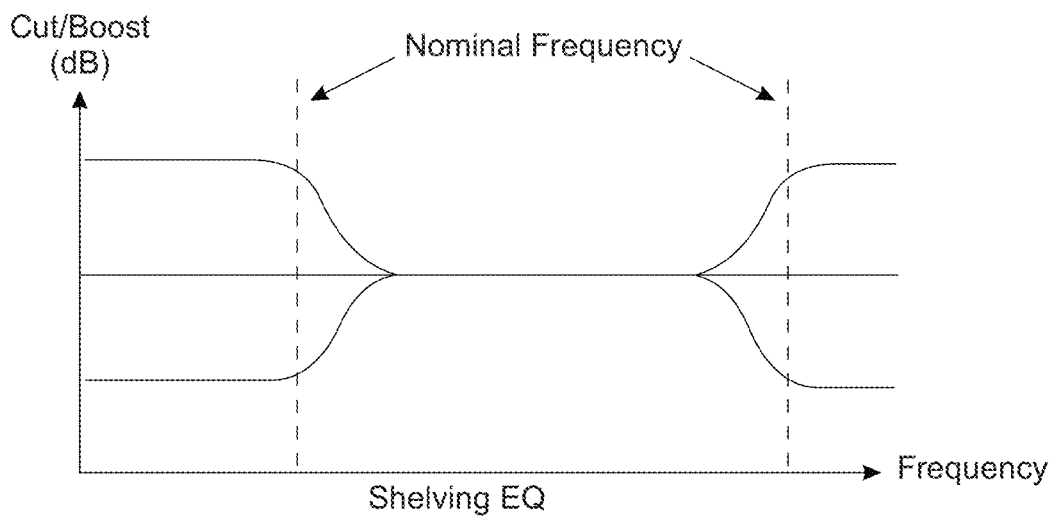
FIG. 5 is an illustrative example of a band boost filter configured to function as a shelf filter produced in accordance with one embodiment of the invention.

In accordance with an embodiment of the invention, a band boost filter is calibrated to function as a high frequency shelf filter (an illustration of which that is not specific to this example is depicted in FIG. 5) based on the above hearing loss and tinnitus assessment. Because patient 2 exhibits unilateral high frequency hearing loss, in this instance the centre frequency is determined as the 3 dB corner frequency—the first point where hearing loss rolls off by 3 dB. The boost ratio is determined in order to boost by a max of +45 dB, the centre frequency (Fc) (taken to be as the 3 dB corner frequency) is identified as 1 kHz, and the bandwith is determined as extending from 1 kHz to the limit of human hearing (approximately 20 kHz). The slope of the filter from the centre frequency is determined as 45 dB over 3 octaves (average of the hearing loss between 1 kHz and 8 kHz), equating to 15 dB/octave. Application of a filter of this type to a patient suffering from this particular hearing loss profile has the effect of normalizing the spectral intensity of the noise that is perceived by the patient. In the event pure white noise is delivered to patient 2 through this filter, patient 2 would perceive the noise as pure white noise.

In a third example, patient 3 presents with a suspected hearing loss and/or tinnitus, and pure tone audiometry is carried out to quantify the type, degree and configuration of hearing (as desctibed above). Psychoacoustic assessment, including Tinnitus Matching (TM), Tinnitus Loudness Matching (TLM) and Minimum Masking Levels (MML) are determined (as described above).

Figure 6:
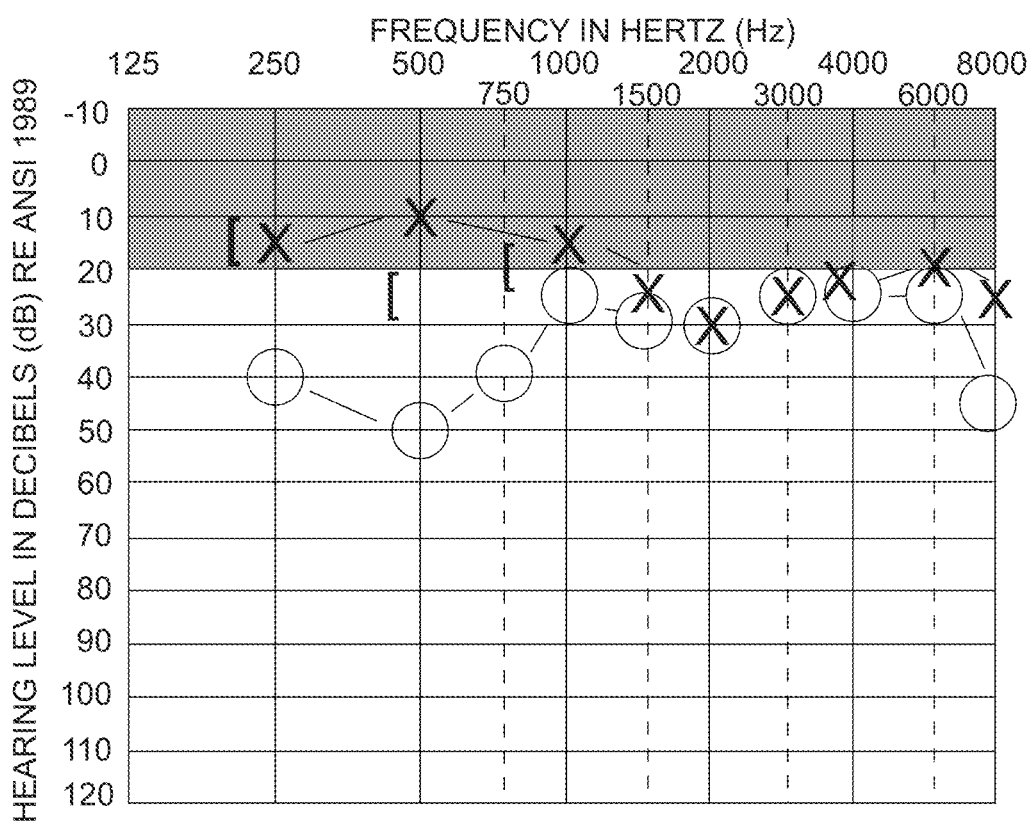
FIG. 6 is a sample audiogram in accordance with patient 3 of example 3.

The results of the audiogram for patient 3 can be seen in FIG. 6 (x=left ear, o=right ear), illustrating bilateral mixed loss—sensorineural loss on the left and mixed loss on the right. This is a comparatively more complex hearing loss profile than that shown by the audiogram of FIG. 1. The left ear exhibits hearing loss as follows: 8 kHz @ 25 dB, 2 kHz @ 20 dB, 250 Hz @ 15 dB. The right ear exhibits hearing loss as follows: 8 kHz @ 45 dB, 2 kHz @ 30 dB, 500 Hz @ 50 dB, 250 Hz @ 40 dB. The results of the psychoacoustic assessment for tinnitus (not shown in FIG. 6) results in tinnitus matched at a pure tone of 15 dB @ 4 kHz on the left ear, and 25 dB @ 2 kHz on the right ear.

In accordance with an embodiment of the invention, a first band boost filter is calibrated to boost certain frequencies of the audio signal to be delivered to the left ear and a second band boost filter is calibrated to function as a hi-lo shelf filter (not shown) for the audio signal to be delivered to the right ear based on the above hearing loss and tinnitus assessment. Based on the audiogram of the left ear, the boost ratio and centre frequency (Fc) may be calculated for the left ear band boost filter. In this example, the boost ratio is set in order to boost by +30 dB, the centre frequency (Fc) identified as 4 kHz (which in this case is also the tinnitus matching frequency). For the right ear, a first Fc (set as 3 dB Corner Frequency) is identified as 1 kHz (this is the first point where hearing loss rolls off by more than 3 dB for low frequencies) and a second Fc (set as another 3 dB Corner Frequency) is identified as 6 kHz (this is the first point where hearing loss rolls off by more than 3 dB for high frequencies). The slope of the low frequency shelf filter is determined as 15 dB/2 octaves (average of the hearing loss between 1 kHz and 250 Hz)=7.5 dB/octave, and the slope of high frequency shelf filter is determined as 20 dB/half octaves (average of the hearing loss between 6 kHz and 8 kHz)=40 dB/octave. Accordingly, at a frequency of 2 kHz, a boost of +15 dB will be applied. Application of a filter of this type to a patient suffering from this particular hearing loss profile has the effect of normalizing the spectral intensity of the noise that is perceived by the patient in both ears. In the event pure white noise is delivered to patient 2 through this filter, patient 2 would perceive the noise as pure white noise.

EXAMPLE 4

A clinical pilot study into the impact of using a method and device in accordance with an embodiment of the invention for the treatment and symptomatic relief from permanent intractable tinnitus, was conducted, and the findings are discussed below.

Materials and Methods

The objective of the study was to determine the impact of acoustic and tactile multi-modal neuromodulation on objective and subjective measures of permanent intractable tinnitus. This was a 16 week study. Participants were screened for 4 weeks, received treatment for 10 weeks and were followed up at 2 weeks post-treatment. The trial was designed to establish baseline figures for the 4-week run-in period, to compare treatment outcomes over 10 weeks with baseline figures and to assess usage and tolerance of the device over the duration of trial. The study was conducted by a Clinical Audiologist who is registered with the Irish Society of Hearing Aid Audiologists (ISHAA) and the Irish Academy of Audiology (IAA), under the clinical supervision of a Senior Consultant Otolaryngologist Head & Neck Surgeon who is a member of the Association for Research in Otolaryngology, European Academy of Otology and Neurotology, Royal Society of Medicing: Otology, Laryngology & Rhinology, Prosper Meniere Society, Irish Otolaryngology Society and the American Auditory Society.

Eligibility of study participants was determined by the inclusion and exclusion criteria, as listed below. Patients were deemed eligible if they complied with the following; the minimum total use of the device should be 30 minutes per day, i.e. 3.5 hours per week; the level of stimulus should be greater than zero; acceptable timing for visit dates: Baseline interview had to be conducted within 4 weeks from the start of the new treatment.

Inclusion Criteria: Aged <65; Suffering from intractable subjective tinnitus for more than 6 months; Tinnitus associated with an age or noise related sensorineural hearing loss; Have English reading, comprehension and written skills; Able and willing to participate in the study for the full 16 weeks duration, Informed consent.

Exclusion Criteria: Ulceration of oral cavity or tongue; oral mucosa or significant intra-oral disease—to mitigate risk of further aggravation of these symptoms; Meniere's Disease—due to the fluctuating hearing loss patients normally present with Hyperacusis—to avoid further aggravation of sensitivity of sound; Current medical legal cases regarding tinnitus or hearing—in order to avoid any conflict of interest; Undergoing any treatment for tinnitus—in order to accurately measure the independent effect of the intervention; Pacemakers—due to potential magnetic interference.

Non-Eligibility and Withdrawals.

Participants who were not deemed eligible at prescreen to take part in this particular study were referred back to their GP and received a formal letter of refusal. Participants who withdrew after commencement of this study were analysed according to the intention-to-treat (ITT) method. Patients were informed that participation in the study was entirely voluntary, and they were free to withdraw from the study at any time without having to give a reason. The recruitment process allowed patients adequate time to fully consider participation.

Minimizing Bias

Bias was minimized through annonomysed participation and the use of objective and subjective gold standard outcome measures.

Treatment

The Pre-Treatment Phase consisted of a four-week run-in period prior to commencement of treatment where baseline measures were obtained and sampled every 2 weeks at Week 0, Week 2 and Week 4. The Treatment Phase consisted of a 10-week period where participants used the device for a recommended 60 minutes per day in their home. All participants' usage of the device was logged on an internal SD reader card. Objective and subjective tests as described above were carried out at the enrollment visit and every two weeks for the duration of study.

Assessment of Outcome Measures and Compliance

Primary outcome measures were assessed across the duration of the study in the clinical environment at 'review' visits. Participant's compliance was measured using data logging methodology and tolerability assessed on completion of the study through a questionnaire.

Subjective Outcome Measures

The Tinnitus Handicap Inventory (THI) is a 25-item self-reporting questionnaire for the measurement of tinnitus. Patients completed THI questionnaires every two weeks, immediately prior to review visits. THI scores are categorized into five grades of severity that range from 'slight' to 'catastrophic'.

Objective Outcome Measures

Tinnitus Matching (TM) is a psychoacoustic assessment, which determines the frequency pitch of the tinnitus. Tinnitus Loudness Matching (TLM) is a psychoacoustic assessment, which determines the intensity of the tinnitus. Minimum Masking Level (MML) is a psychoacoustic assessment, which determines the lowest level of noise required to mask the tinnitus [45]. Patients underwent TM, TLM and MML assessments every two weeks at review visits.

Materials

An auditory and tactile stimulation device in accordance with an embodiment of the invention was used in the study. The non-invasive device was capable of simultaneously delivering auditory stimuli to the ears through hi-fidelity headphones and tactile patterns through an array of thirty-two transcutaneous electrical stimulators on the tongue.

In this study, the device was used to deliver an auditory stimulus that included broad-spectrum sound (referred to herein as "coloured noise") and relaxing music that were band-boost filtered to match the patients audiogram. Simultaneous to the auditory stimulus, the device presented transcutaneous electrical stimulation of the anterio-dorsal surface of the tongue, where the electrical stimulus was a spatio-temporal encoded pattern that represented the instantaneous frequency-domain coefficients of the auditory stimulus.

Results and Analysis

Analysis Population and Compliance

Statistical analysis was carried out on data from the Intent-To-Treat population. Participant data was deemed eligible if they met the following compliance and minimum appliance requirements: Minimum total use of 30 mins per day or 3.5 hours per week; Minimum level of stimulus; greater than zero; Review visits within one week of scheduled dates.

Demographics and Baseline Characteristics

Baseline measures and basic demographic data (age/gender) were obtained during the pre-treatment phase.

Summary tables and figures are presented below for each characteristic:

TABLE 2

Age - summary statistics

| | N | Mean | Std. Dev. | Min | Max |
|---|---|---|---|---|---|
| Age | 54 | 47 | 11 | 21 | 64 |

TABLE 3

Age Distribution

| Age Category | Frequency | Percentage | Cum. Percentage |
|---|---|---|---|
| <30 | 4 | 7.41 | 7.41 |
| 30-39 | 11 | 20.37 | 27.78 |
| 40-49 | 16 | 29.63 | 57.41 |
| 50-59 | 15 | 27.78 | 85.19 |
| 60-69 | 8 | 14.91 | 100.00 |
| Total | 54 | 100.00 | |

Average age of the group was 47. The youngest patient was 21 and the eldest was 64. Over half of the patients (57%) were under the age of 50. 34 (63%) patients were male and 20 (37%) patients were female.

Hearing Loss Profile

Hearing loss profile was measured for left and right ear individually using GN Otometrics Madsen Astera Clinical Audiometer, calibrated in accordance with BS EN 60645-1 (IEC 60645-1) and the relevant BS EN ISO 389 (ISO 389) series standards. Hearing loss was classified according to severity: Normal, Mild, Mild to Moderate, Moderate, Moderate to Severe, Severe. The distribution of severity is summarised in the following tables.

TABLE 4

Hearing Loss Profile at Screening - Left Ear

| Grade | Freq | Percentage | Cum. Percentage |
|---|---|---|---|
| Normal | 4 | 7.41 | 7.41 |
| Mild | 19 | 35.19 | 42.59 |
| Mild to Moderate | 25 | 46.30 | 88.89 |
| Moderate | 4 | 7.41 | 96.30 |
| Moderate to Severe | 1 | 1.85 | 98.15 |
| Severe | 1 | 1.85 | 100.00 |
| Total | 52 | 100.00 | |

TABLE 5

Hearing Loss Profile at Screening - Right Ear

| Grade | Freq | Percentage | Cum. Percentage |
|---|---|---|---|
| Normal | 2 | 3.77 | 3.77 |
| Mild | 20 | 37.74 | 41.51 |
| Mild to Moderate | 27 | 50.94 | 92.45 |

TABLE 5-continued

Hearing Loss Profile at Screening - Right Ear

| Grade | Freq | Percentage | Cum. Percentage |
|---|---|---|---|
| Moderate | 4 | 7.55 | 100.00 |
| Moderate to Severe | 0 | 0.00 | |
| Severe | 0 | 0.00 | |
| Total | 50 | 100.00 | |

In the majority of cases the severity of hearing loss at screening ranged between mild and moderate. Very few cases were diagnosed as severe.

Tinnitus Profile

The tinnitus profile of patients were measured at screening using the following scores: THI, MML, TLM and TM. Summary statistics are shown in the following table.

TABLE 6

Tinnitus Scores at screening - summary statistics

| Score | N | Mean | Std. dev. | Min | Max |
|---|---|---|---|---|---|
| THI | 54 | 40.1 | 22.4 | 6 | 94 |
| MML | 54 | 50.8 | 17.1 | 15 | 85 |
| TM | 54 | 6518 | 3387 | 250 | 12500 |
| TML | 54 | 42.9 | 19.7 | 10 | 85 |

Analysis

The Impact of acoustic and tactile multi-modal neuromodulation on objective and subjective measures of permanent intractable tinnitus was determined by measuring the change in the THI, MML, TLM and TM scores over time. Scores were obtained at screening V0 and Baseline V2 and every 2 weeks for duration of study. Comparisons were made between Baselines V2 (Week 4/1$^{st}$ Week of treatment) and V7 (Week 14/10 weeks of treatment) for main effect and between Baseline V2 and V4 (Week 8/4 weeks of treatment) for interim effect. A placebo/context effect was explored as a comparison between screening visit V0 and baseline V2, where participants have not yet received treatment. Short term effects of treatment were measured as comparison between last week of treatment V7 (Week 14/10 Weeks of treatment) and V8 (Week 16/2 weeks post treatment).

Boxplots and repeated ANOVA were run for all sampled measures to determine statistical significance. Paired t-tests were carried out to compare main effect (change between baseline V2 and V7 (Week 14/10 Weeks of treatment)) and interim effect (change between baseline V2 and V4 (Week 8/4 Weeks of treatment).

The potential placebo/context effect was analysed in an exploratory manner comparing measures at V0 and Baseline V2. This was a 4 week run-in period in which intervention is not administered, but some beneficial effect may have been observed due to the subjective nature of tinnitus. Paired t-tests compared Screening visit V0 and Baseline V2 to test evidence of potential placebo/context effect.

Minimum Masking Level (MML)

Figure 7:
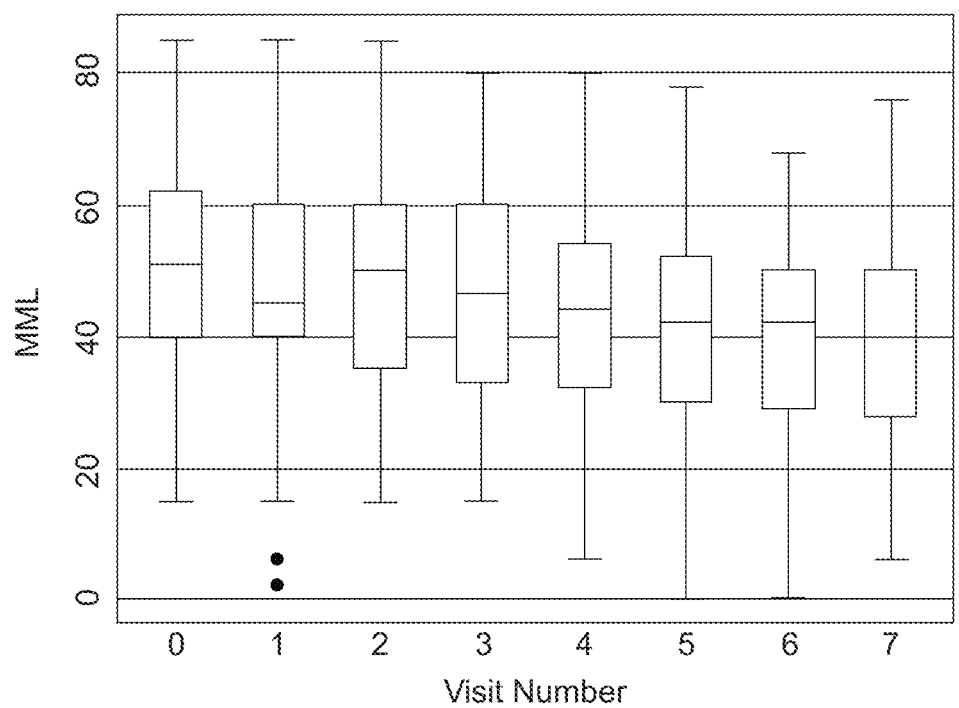
FIG. 7 is a boxplot of MML from Screening Visit (V0/Week 0) to End of Treatment Visit (V7/Week 14) in accordance with the study described in example 4.

Change in MML score over time was shown in FIG. 7. Overall repeated ANOVA was statistically significant (p-value <0.001). Paired t-test comparison between Baseline V0 and V7 (Week 14/10 Weeks of treatment) was also significant (p-value <0.001). MML score decreased from an average value of 47.4 (SD=2.54, 95% CI: 42.3-52.6, N=39) at Baseline V2 to 38.8 (SD=2.7, 95% CI: 33.4-43.34, N=39) at V7 (Week 14/10 Weeks of treatment). Interim effect, (average change in MML from baseline V2 to V4 (Week 8/4 Weeks of treatment), was also significant (p-value=0.0088), it decreased from 48.15 (SD=2.69, 95% CI: 42.66-53.64, N=33) at Baseline V0 to 43.79 (SD=3.13, 95% CI: 37.4-50.16, N=33) at V4 (Week 8).

There was some evidence of a placebo/context effect for the MML score, but it was not significant (p-value=0.01). Between screening visit V0 and baseline V2 the average MML score changed from 50.8 (SD 2.3) V0 to 46.7 (SD 2.2) (N=54) V2.

Tinnitus Loudness Matching (TML)

Figure 8:
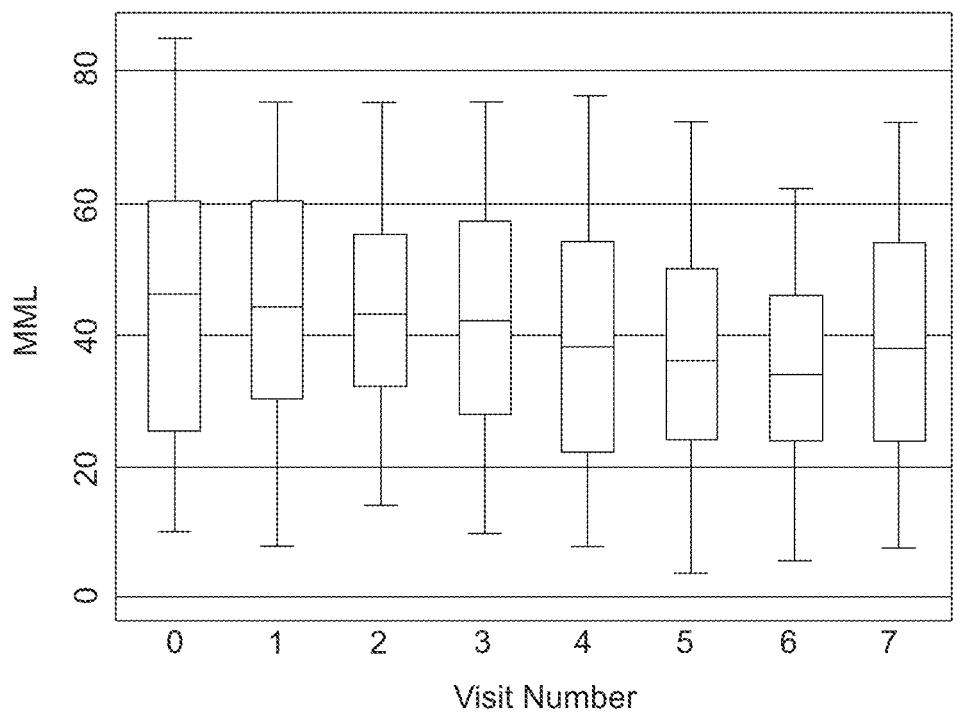
FIG. 8 is a boxplot of TLM from Screening Visit (V0/Week 0) to End of Treatment Visit (V7/Week 14) in accordance with the study described in example 4.

The change of TLM score over time is shown in FIG. 8. The overall repeated ANOVA is statistically significant (p-value <0.001). The paired t-test comparison between V2 Baseline and V7 (Week 14/10 Weeks of treatment) was also significant (p-value=0.001). The TLM score decreased from an average value of 45.3 (SD=2.5, 95% CI: 40.2-50.4, N=39) at Baseline (V2) to 38.1 (SD=2.75, 95% CI: 32.5-43.6, N=33) at V7 (Week 14/10 Weeks of treatment). Interim effect, (average change in TML from baseline V2 to V4 (Week 8/4 Weeks of treatment)), was also significant (p-value=0.045), it decreased from 44.63 (SD=2.61, 95% CI: 39.31-50, N=33) at Baseline V2 to 40.18 (SD=3.28, 95% CI: 33.5-46.85, N=33) V4 (Week 8/4Weeks of treatment). There was no evidence of a placebo/context effect for TLM score. Average change between screening visit V0 and Baseline V2 was less than 1 point, changing from 42.9 (SD 2.68) to 43.4 (SD 2.1), and was not significant.

Tinnitus Handicap Inventory (THI)

Figure 9:
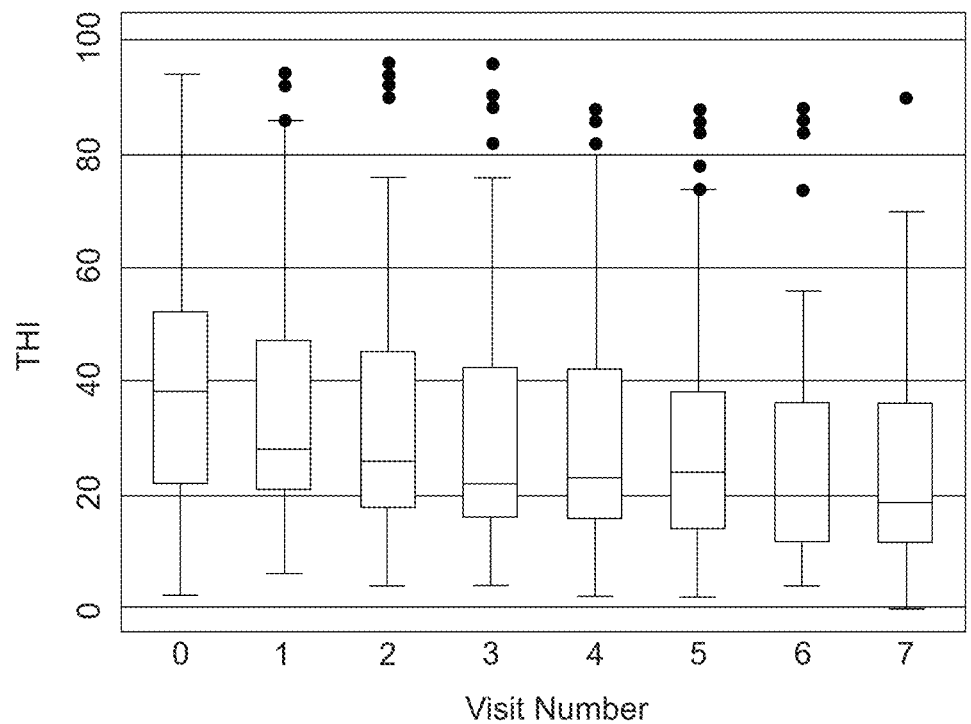
FIG. 9 is a boxplot of THI from Screening Visit (V0/Week 0) to End of Treatment Visit (V7/Week 14) in accordance with the study described in example 4.

Change in THI score over time is shown in FIG. 9. Overall repeated ANOVA was statistically significant (p-value <0.001). Paired t-test comparison between Baseline V2 and V7 (Week 14/10 Weeks of treatment) was also determined to be significant (p-value <0.001). THI score decreased from an average value of 34.3 (95% CI: 27.3-41.2, N=46) at Baseline V0 to 24.9 (95% CI: 19.8-30.7, N=42) at V7 (Week 14/10 Weeks of treatment). Interim effect (average change in THI from baseline V2 to V4 (Week 8/4 Weeks of treatment), was also significant (p-value=0.0052), decreased from 34.42 (95% CI: 27.5-41.3, N=50) at Baseline V2 to 31.12 (95% CI: 24.2-38.1, N=50) at V4 (Week 8/4 Weeks of treatment). Significant placebo/context effect was determined for THI score. Average THI score dropped from 41.1 (SD 3.04) to 34.2 (SD 3.2) (N=54) from V0 screening visit to V2 baseline visit and the change was statistically significant (p-value <0.001).

Tinnitus Matching

Figure 10:
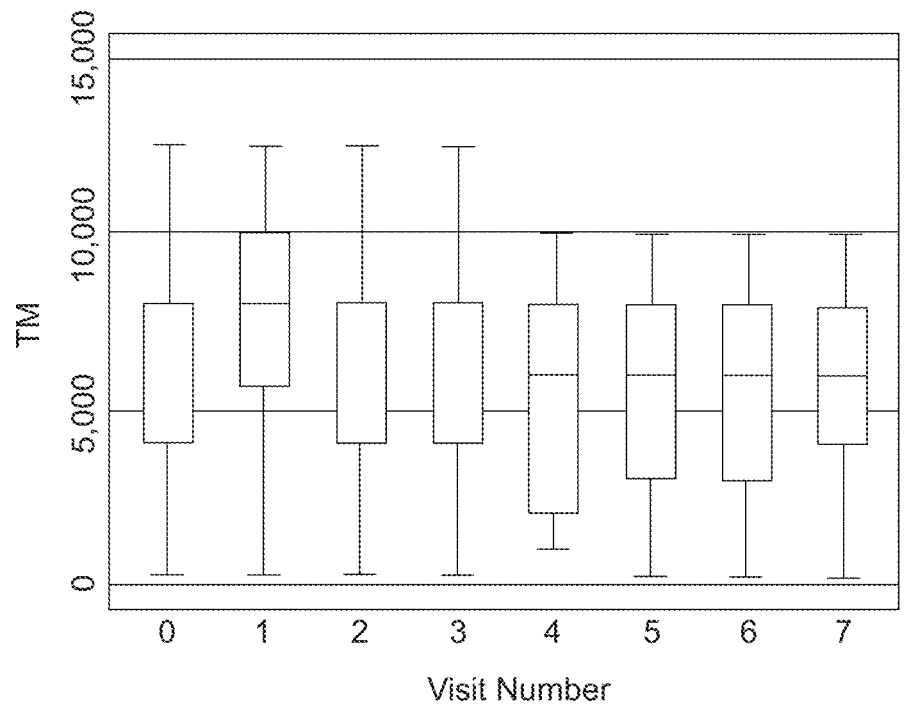
FIG. 10 is a boxplot of TM from Screening Visit (V0/Week 0) to End of Treatment Visit (V7/Week 14) in accordance with the study described in example 4.

Change of TM score over time is shown in FIG. 10. Overall repeated ANOVA showed some trend of decreasing values, but was not significant. Summary values for each visit are presented in the following table.

TABLE 7

TM Score - Summary Statistics

| Visit | N | Mean | Std. Dev. | Min | Max |
|---|---|---|---|---|---|
| 0 | 54 | 6518 | 3387 | 250 | 12500 |
| 1 | 42 | 7395 | 3437 | 250 | 12500 |
| 2 | 54 | 6199 | 3319 | 250 | 12500 |
| 3 | 40 | 6343 | 3380.1 | 250 | 12500 |
| 4 | 33 | 5454 | 3327 | 1000 | 10000 |
| 5 | 37 | 5574 | 3155 | 250 | 10000 |
| 6 | 40 | 5756 | 3105.8 | 250 | 10000 |
| 7 | 39 | 5814 | 3093 | 250 | 10000 |

Discussion

This study demonstrates early evidence of tangible efficacy and suggests that this novel intervention is a promising development in the treatment of tinnitus. The patient group demonstrated a statistically significant mean improvement in objective measures, exhibiting a reduction of 8.6 dB in Minimum Masking Level and 7.2 dB in Tinnitus Loudness Matching between Baseline Visit (V2/Week 4) and End of Treatment Visit (V7/Week 14). These results compare favorably to other studies using similar objective measures [neuromonics 7.68 dB reduction @ 2 months]. Similarly, the patient group demonstrated a statistically significant improvement in the THI subjective measure. This is a particularly significant outcome, given that, unlike other treatments, the intervention being assessed here does not include psychological counseling. This compares favorably to studies involving other stand-alone (without counseling) technologies [ANM].

Figure 11:
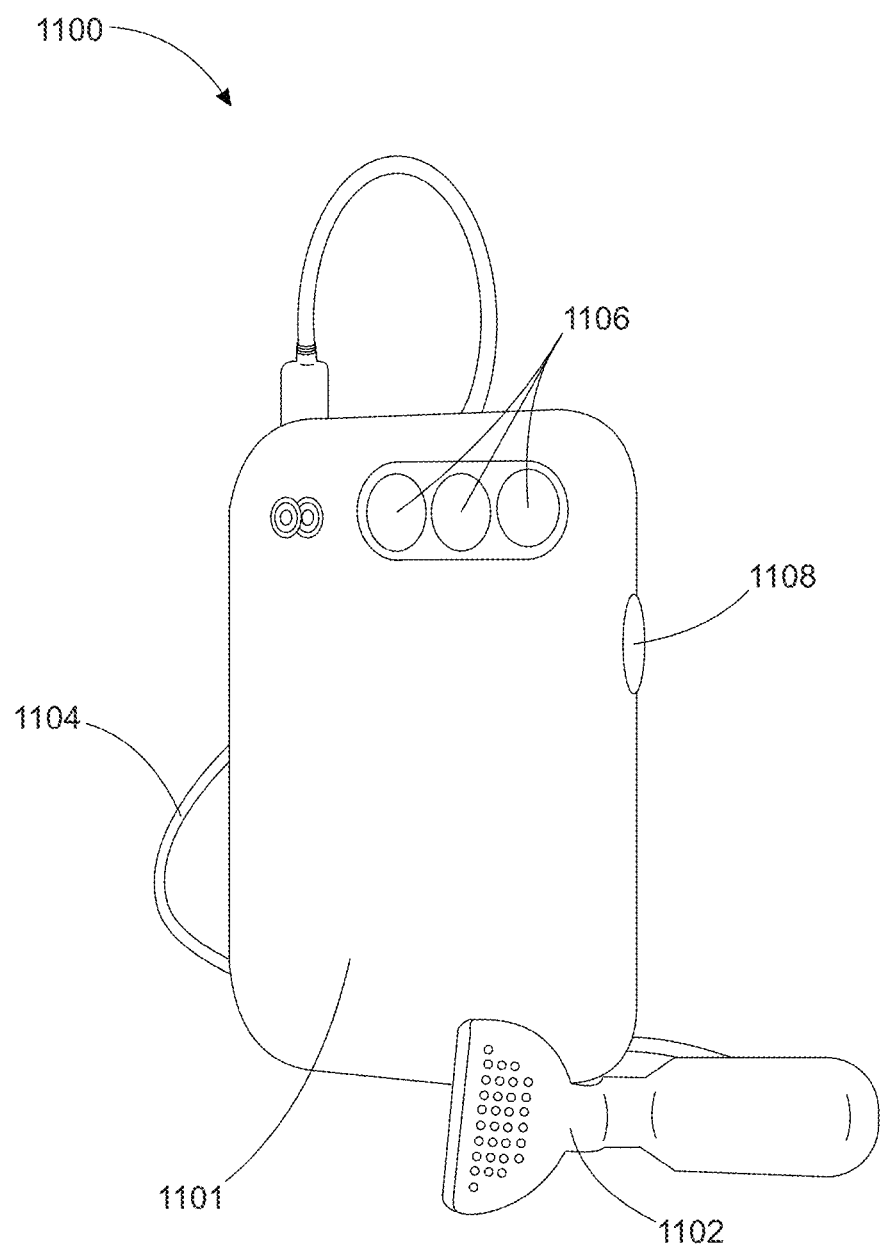
FIG. 11 is a depiction of a system in accordance with one embodiment of the invention.
Figure 12:
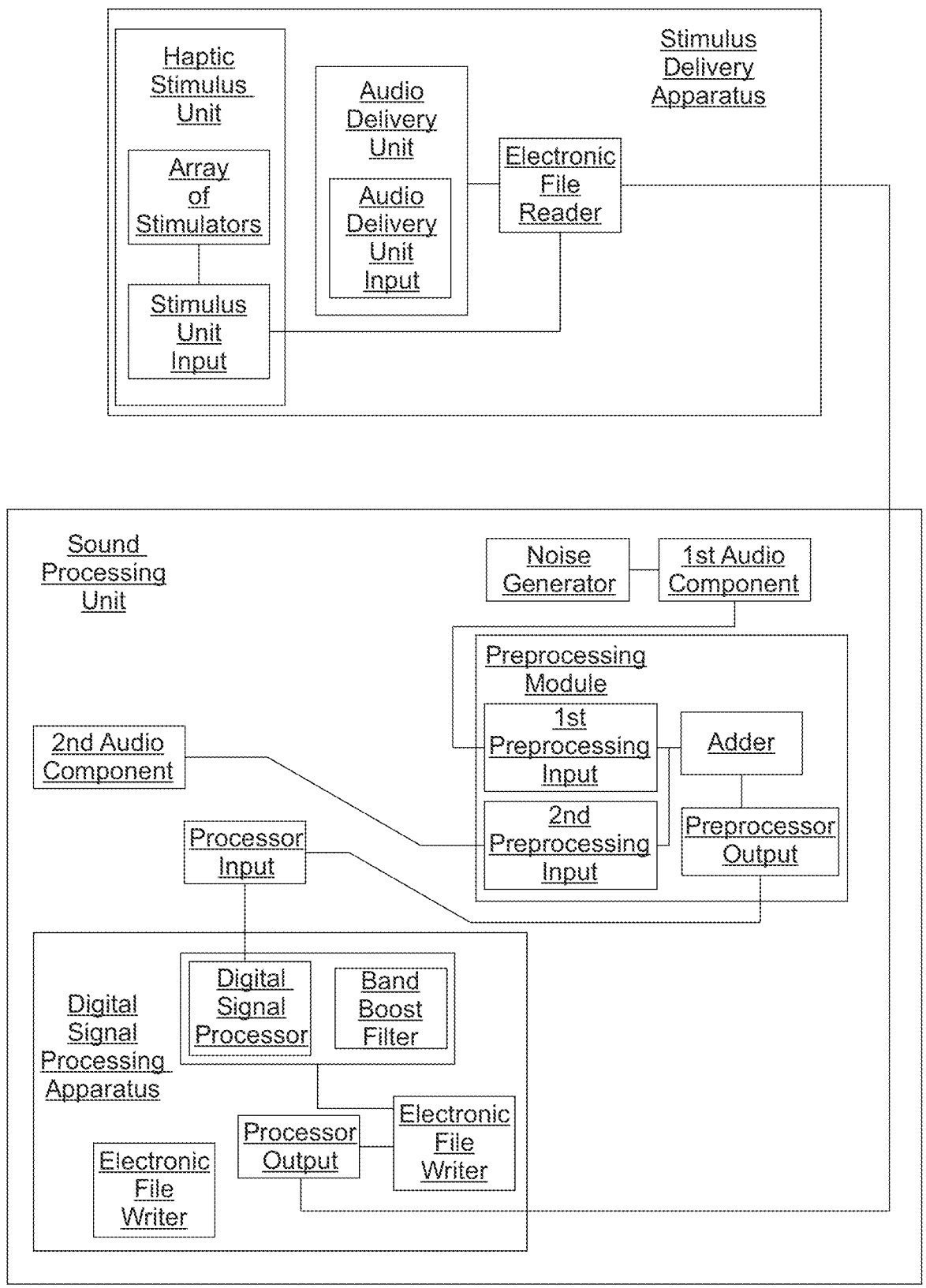
FIG. 12 is a diagrammatic view of a system in accordance with one embodiment of the invention.
Figure 13:
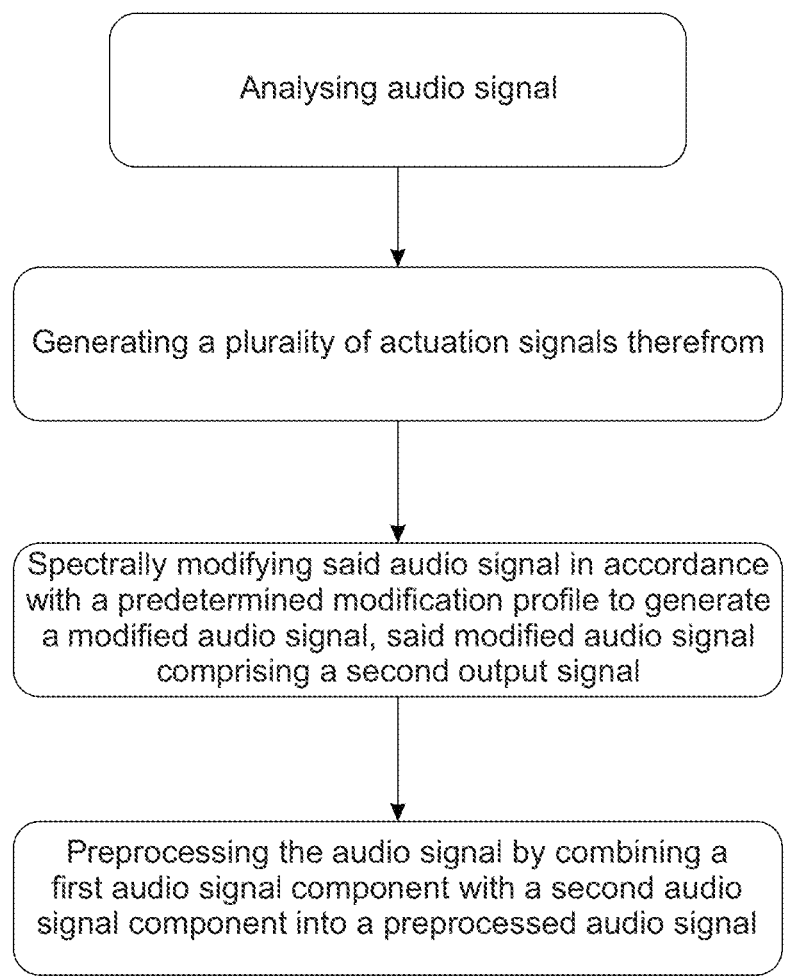
FIG. 13 is a flow chart of a method of using a system in accordance with one embodiment of the invention.
Figure 14:
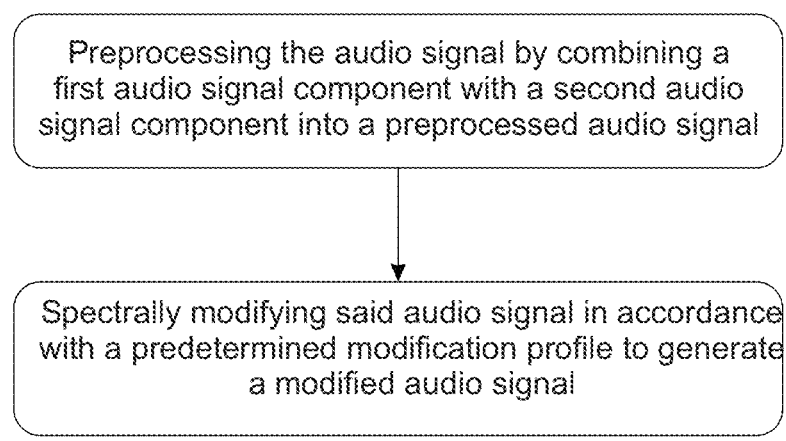
FIG. 14 is a flow chart of another method of using a system in accordance with one embodiment of the invention.

Referring to FIG. 11, there is depicted a system in accordance with one embodiment of the invention. The system comprises a stimulus delivery apparatus 1100. The apparatus comprises a haptic stimulus unit 1102 connected to the apparatus body 1101 by way of connecting cable 1104 and an audio stimulus unit (not shown). Playback of the concurrent, complementary audio signal and haptic stimulus unit actuation signals may be controlled by interface buttons 1106 and volume control 1108. In this embodiment of the invention, a digital signal processor is be comprised in a separate digital signal processing apparatus (not shown), and the stimulus delivery apparatus 1100 comprises an electronic file reader for reading electronic files produced by said digital signal processing apparatus, for converting said files into an audio signal and a plurality of haptic stimulus unit actuation signals, and for delivering said signals to said audio delivery unit and said haptic stimulus unit 1102 respectively.

In an alternative embodiment, the system may comprise a single apparatus comprising all elements of the invention, and the digital signal processor is configured for dynamically and concurrently producing a modified audio signal and a plurality of haptic stimulus apparatus actuation signals from an input audio signal.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A tinnitus treatment system comprising a sound processing unit, a haptic stimulus unit and an audio delivery unit:

wherein said sound processing unit comprises:

a processor input configured for receiving an audio signal, the audio signal comprising a first audio component and a second audio component; and a digital signal processor configured to analyse said audio signal and generate a plurality of actuation signals therefrom which are representative of said audio signal, the digital signal processor further configured to spectrally modify said audio signal in accordance with a predetermined modification profile to generate a modified audio signal, wherein the predetermined modification profile is based on an inversion of an audiogram of a patient suffering from tinnitus, wherein the inversion of the audiogram normalizes a spectral intensity of the audio signal;

wherein said haptic stimulus unit comprises:

an array of stimulators each of which is independently actuated to apply a tactile stimulus to a subject; and a stimulus unit input configured for receiving the plurality of actuation signals generated by said digital signal processor and directing individual actuation signals to individual stimulators; and wherein said audio delivery unit comprises an audio delivery unit input configured for receiving the modified audio signal generated by said digital signal processor.

2. The system of claim 1, wherein the system comprises a digital signal processing apparatus and a stimulus delivery apparatus, further wherein the digital signal processing apparatus comprises:

the digital signal processor; and an electronic file writer configured for storing said generated actuation signals and said modified audio signal in an electronic file format; and wherein the stimulus delivery apparatus comprises:

said haptic stimulus unit;

said audio delivery unit; and an electronic file reader configured for reading electronic files produced by said digital signal processing apparatus, configured for converting said files into an audio signal and a plurality of actuation signals, and configured for delivering said signals to said audio delivery unit and said haptic stimulus unit respectively.

3. The system of claim 1, wherein the sound processing unit further comprises a preprocessing module, the preprocessing module comprising:

a first preprocessor input configured for receiving a first audio signal component;

a second preprocessor input configured for receiving a second audio signal component;

an adder, configured for combining the first audio signal component with the second audio signal component into a preprocessed audio signal, and a preprocessor output, configured for delivering the preprocessed audio signal to the processor input.

4. The system of claim 3, wherein the second audio signal component is capable of holding an attention of a human listener, and is optionally a recording of a musical piece or a recording of human speech.

5. The system of claim 1, wherein the digital signal processor further comprises a band boost filter calibrated in accordance with the predetermined modification profile, and wherein the digital signal processor is operable to spectrally modify said audio signal by passing said audio signal through said band boost filter to produce said modified audio signal.

6. The system of claim 1, wherein the modified audio signal comprises at least a first component signal which occupies a spectral bandwidth that spans a spectral range over which the patient's hearing is impaired.

7. The system of claim 6, wherein the first component signal occupies a spectral bandwidth that extends beyond the spectral range over which the patient's hearing is impaired by at least one octave, more preferably extending below the minimum frequency of hearing loss and extending above the maximum frequency of hearing loss each by about half an octave, and preferably extending below the minimum frequency of hearing loss and extending above the maximum frequency of hearing loss each by about quarter of an octave.

8. The system of claim 1, wherein the modified audio signal occupies a spectral bandwidth such that the modified audio signal, when listened to by said patient elicits the perception of an audio signal comprising at least a white noise component to said signal.

9. The system of claim 1, wherein the modified audio signal comprises at least a first component signal that occupies a spectral bandwidth of between 2 kHz and 6 kHz, between 500 Hz and 8 kHz, between 125 Hz and 20 kHz, or between 125 Hz and 40 kHz.

10. A tinnitus treatment system comprising a sound processing unit comprising a preprocessing module, wherein the preprocessing module comprises:
   a first preprocessing input configured for receiving a first audio signal component;
   a second preprocessing input configured for receiving a second audio signal component;
   an adder, configured for combining the first audio signal component with the second audio signal component into a preprocessed audio signal, and
   a preprocessor output, configured for delivering the preprocessed audio signal to a processor input of the sound processing unit; and
   wherein the sound processing unit further comprises:
      a processor input configured for receiving the preprocessed audio signal output from the preprocessing unit;
      a digital signal processor operable to spectrally modify said preprocessed audio signal in accordance with a predetermined modification profile to produce a modified audio signal, wherein the predetermined modification profile is based on an inversion of an audiogram of a patient suffering from tinnitus, wherein the inversion of the audiogram normalizes a spectral intensity of the audio signal;
      a processor output configured for receiving said modified audio signal from said digital signal processor.

11. The system of claim 10, further comprising a noise generator, wherein the noise generator is configured to generate an audio signal and deliver said audio signal to said first preprocessor input.

12. The system of claim 10, wherein the digital signal processor further comprises a band boost filter calibrated in accordance with the predetermined modification profile, and wherein the digital signal processor is operable to spectrally modify said audio signal by passing said audio signal through said band boost filter to produce said modified audio signal.

13. The system of claim 10, wherein the modified audio signal comprises at least a first component signal which occupies a spectral bandwidth that spans a spectral range over which the patient's hearing is impaired.

14. The system of claim 13, wherein the first component signal occupies a spectral bandwidth that extends beyond the spectral range over which the patient's hearing is impaired by at least one octave, more preferably extending below the minimum frequency of hearing loss and extending above the maximum frequency of hearing loss each by about half an octave, and preferably extending below the minimum frequency of hearing loss and extending above the maximum frequency of hearing loss each by about quarter of an octave.

15. The system of claim 10, wherein the modified audio signal occupies a spectral bandwidth such that the modified audio signal, when listened to by said patient elicits the perception of an audio signal comprising at least a white noise component to said signal.

16. The system of claim 10, wherein the modified audio signal comprises at least a first component signal that occupies a spectral bandwidth of between 2 kHz and 6 kHz, between 500 Hz and 8 kHz, between 125 Hz and 20 kHz, or between 125 Hz and 40 kHz.

17. The system of claim 10, wherein the second audio signal component is capable of holding an attention of a human listener, and is optionally a recording of a musical piece or a recording of human speech.

18. A method of processing an audio signal, comprising:
   analysing said audio signal;
   generating a plurality of actuation signals therefrom which are representative of said audio signal, said plurality of actuation signals comprising a first output signal and being suitable for actuation of an electrode array; and
   spectrally modifying said audio signal in accordance with a predetermined modification profile to generate a modified audio signal, wherein the predetermined modification profile is based on an inversion of an audiogram of a patient suffering from tinnitus, wherein the inversion of the audiogram normalizes a spectral intensity of the audio signal, said modified audio signal comprising a second output signal,
   wherein the output signals are transmitted to signal output devices or converted into an electronic file format and stored electronically;
   and wherein the method optionally further comprises the step of preprocessing the audio signal by combining a first audio signal component with a second audio signal component into a preprocessed audio signal.

19. A method of processing an audio signal comprising:
   preprocessing the audio signal by combining a first audio signal component with a second audio signal component into a preprocessed audio signal, and
   spectrally modifying said audio signal in accordance with a predetermined modification profile to generate a modified audio signal,
      wherein the predetermined modification profile is based on an inversion of an audiogram of a patient suffering from tinnitus, wherein the inversion of the audiogram normalizes a spectral intensity of the audio signal, and said first audio signal occupies a spectral bandwidth that spans a spectral range over which the patient's hearing is impaired.

* * * * *